United States Patent
Ooura et al.

(10) Patent No.: US 8,366,896 B2
(45) Date of Patent: Feb. 5, 2013

(54) CAPILLARY ELECTROPHORESIS DEVICE

(75) Inventors: Takeshi Ooura, Hitachinaka (JP); Ryoji Inaba, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1066 days.

(21) Appl. No.: 12/130,330

(22) Filed: May 30, 2008

(65) Prior Publication Data

US 2008/0296160 A1 Dec. 4, 2008

(30) Foreign Application Priority Data

Jun. 1, 2007 (JP) ................................. 2007-146404

(51) Int. Cl.
*G01N 27/447* (2006.01)
(52) U.S. Cl. ....................... 204/451; 204/601; 435/288.3
(58) Field of Classification Search .......... 204/451–454, 204/601–605; 24/163, 186, 187, 593.1, 595.1; 277/388; 435/283.1–309.4
See application file for complete search history.

(56) References Cited

U.S. PATENT DOCUMENTS

| | | |
|---|---|---|
| 2003/0221965 A1 | 12/2003 | Seino et al. |
| 2004/0043479 A1* | 3/2004 | Briscoe et al. ............. 435/288.5 |
| 2004/0112749 A1 | 6/2004 | Shibasaki et al. |
| 2004/0173460 A1 | 9/2004 | Yamamoto et al. |

FOREIGN PATENT DOCUMENTS

| | | |
|---|---|---|
| JP | 2003-344357 A | 12/2003 |
| WO | WO 02/079773 A1 | 10/2002 |
| WO | WO 02/090968 A1 | 11/2002 |

OTHER PUBLICATIONS

Japanese Office Action issued in Japanese Patent Application No. 2007-146404, dated Jun. 7, 2011.

* cited by examiner

*Primary Examiner* — Kaj K Olsen
*Assistant Examiner* — Kourtney S Carlson
(74) *Attorney, Agent, or Firm* — McDermott Will & Emery LLP (57) ABSTRACT

Provided is a capillary electrophoresis device including a holder preventing a septum from coming off when a capillary is pulled out, and also allowing containers to be taken out in any order. In the capillary electrophoresis device for separating and analyzing a sample such as a DNA and a protein by electrophoresis, the holder includes: a septum having a capillary hole through which a capillary penetrates; a container for storing a solution; and a container-accommodation unit for accommodating the container. A hole formed in the septum engages with an engagement portion formed on the container, and thereby the septum is held to cover the container.

22 Claims, 6 Drawing Sheets

CAPILLARY ELECTROPHORESIS DEVICE

BACKGROUND OF THE INVENTION

1. Field of the Invention

The present invention relates to a capillary electrophoresis device for separating and analyzing a sample such as a DNA and a protein by electrophoresis. Particularly, the present invention relates to a holder for holding a solution such as a sample solution, a buffer solution, an assy solution, and a rinse.

2. Description of the Related Art

A solution for a sample, an assy, a buffer, a rinse or the like used in a capillary electrophoresis device is stored in a container hermetically sealed by a septum. A capillary comes into contact with the liquid in the container through a hole opened in the septum.

The septum is made of an elastic material. When the capillary penetrates into the hole in the septum, the hole contracts by an elastic force, and thus the septum hermetically seals the surrounding of the capillary. When the capillary is inserted into the hole in the septum, a driving force is needed to push the capillary into the hole against a friction force between the capillary and the hole. Additionally, when the capillary is pulled out from the hole in the septum, a driving force is needed to pull out the capillary against the friction force. When the capillary is pulled out from the hole in the septum, the septum may be also lifted from the container due to the friction force between the capillary and the hole. When the friction force is large, not only the septum but also the container may be lifted together with the capillary.

In order to solve this problem, a stripper has been used conventionally as described in WO2002/079773 or the like. When a capillary is pulled out from a septum, the stripper prevents the septum and its container from lifting up by pressing the septum down.

Moreover, a capillary electrophoresis device described in WO2002/090968 is provided with a guide which prevents various containers, such as a buffer container and a microtiter plate for storing a sample, from being taken off from a container-accommodation unit, when a capillary is inserted into or pulled out from the various containers.

SUMMARY OF THE INVENTION

In a capillary electrophoresis device described in WO2002/079773, the stripper continuously applies a downward force to an autosampler, while being in contact with the autosampler. The autosampler is driven by, for example, a stepper motor. When the stepper motor is being excited, the autosampler does not move owing to a holding torque of the stepper motor. Nevertheless, when a power supply of the electrophoresis device is turned off, the stepper motor is released from the excitation state, and thus the holding torque is ceased. At this point, the autosampler may be pushed downward by the stripper in some cases.

In the capillary electrophoresis device described in WO2002/090968, the guide hinders the container from being attached to the container-accommodation unit in a direction in which the capillary is inserted or pulled (hereinafter, referred to as a capillary-drawing direction). For this reason, the container is attached to the container-accommodation unit from a side surface of the container-accommodation unit in a direction perpendicular to the capillary-drawing direction. As a result, the direction in which the container is attached is limited, which makes the handling of the capillary electrophoresis device inconvenient.

An object of the present invention is to provide a capillary electrophoresis device which allows a capillary to be easily pulled out from a septum.

The present invention relates to a capillary electrophoresis device for separating and analyzing a sample such as a DNA and a protein by electrophoresis, and also relates to a holder for the capillary electrophoresis device. The holder includes: a septum having a capillary hole through which a capillary penetrates; a container for storing a solution; and a container-accommodation unit for accommodating the container. An engagement portion formed on the septum engages with an engagement portion formed on the container, and thereby the septum is held to cover the container.

Moreover, the containers are accommodated into the container-accommodation unit in a vertical direction, and thereby each of the containers can be disposed into any position in any order.

According to the present invention, when the capillary is pulled out, the septum is prevented from coming off. Moreover, the containers are taken out in any order.

DETAILED DESCRIPTION OF THE PREFERRED EMBODIMENTS

Figure 1:
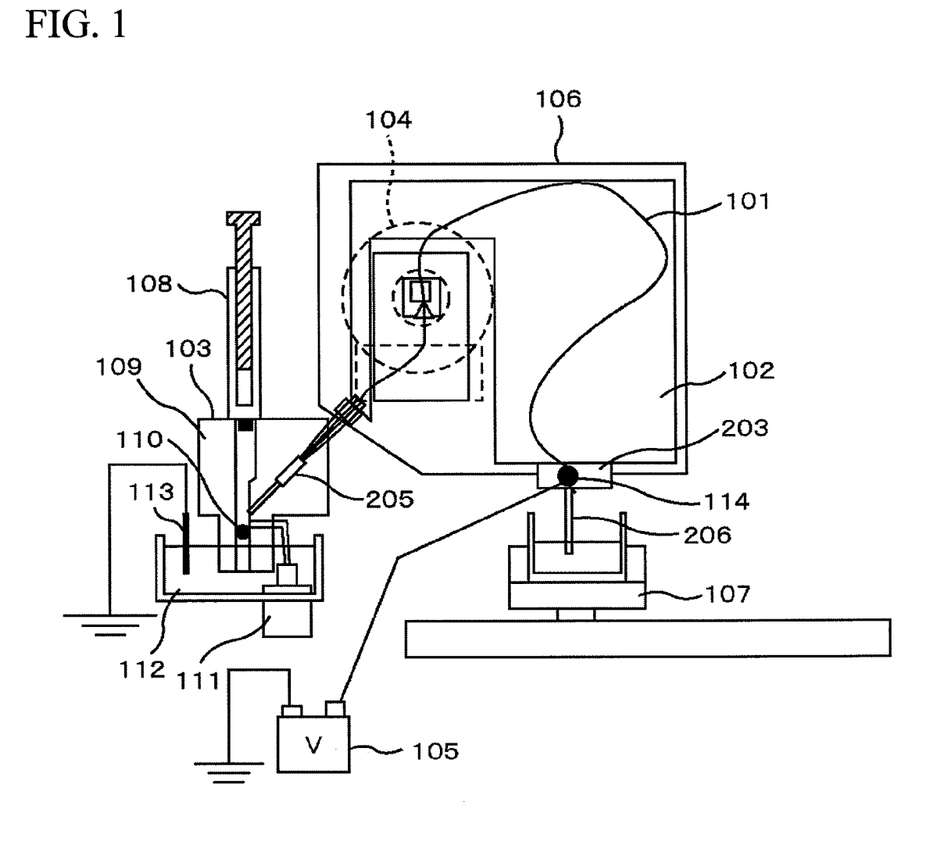
FIG. 1 shows an overview of a capillary electrophoresis device according to an embodiment of the present invention.

FIG. 1 shows an overview of a capillary electrophoresis device according to an embodiment of the present invention. The capillary electrophoresis device of this embodiment includes: a capillary array 102 having a single capillary 101 or the multiple capillaries 101; a pump mechanism 103 for injecting the capillary 101 with a polymer; an optical system 104 which irradiates a sample in the capillary 101 with light to detect fluorescence from the sample; a high-voltage power supply 105 for applying a high voltage to the capillary 101; an oven 106 for keeping a temperature of the capillary 101 constant; and an autosampler 107 for transferring a container storing a sample, solution, and the like therein.

The capillary 101 is a replaceable member, and replaced with a fresh capillary 101 when a measurement method is changed, when the capillary 101 is fractured or when the quality thereof is deteriorated. The capillary 101 is configured of a glass tube with an inner diameter of several tens to several hundreds of micrometer, and an outer diameter of several hundreds of micrometer. The surface of the capillary 101 is coated with polyimide. The capillary 101 is filled with separation media for providing a migration time difference during electrophoresis. Some types of separation media have fluidity, and others do not. In this embodiment, a polymer having fluidity is used.

Figure 2:
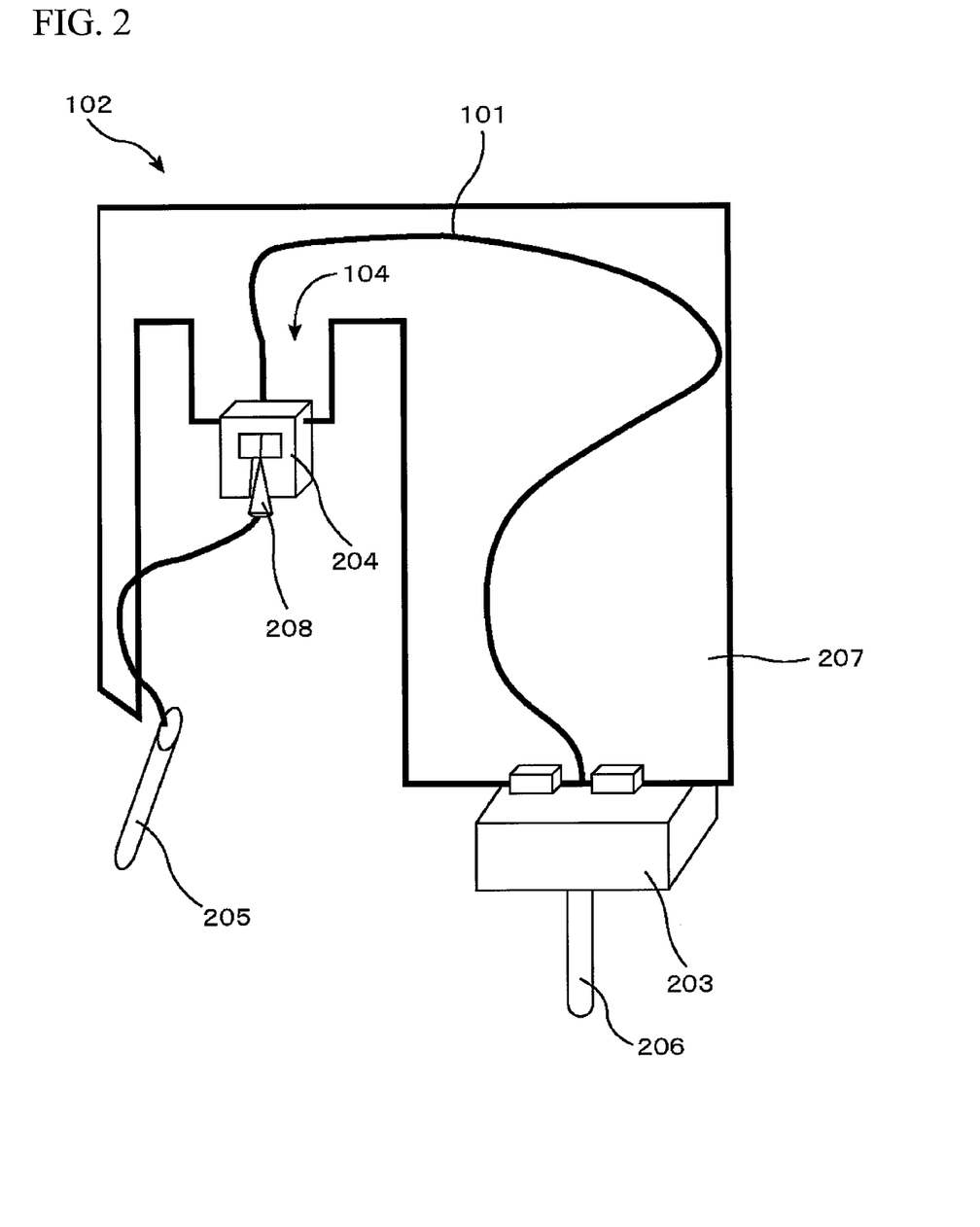
FIG. 2 shows a configuration of a capillary array in the capillary electrophoresis device according to the embodiment.

A capillary head 205 is provided to one end of the capillary 101, and a capillary cathode electrode 206 is formed at the other end of the capillary 101. The capillary head 205 is formed by bundling the end of capillary 101, and functions to connect the pump mechanism 103 with the capillary 101. The capillary cathode electrode 206 comes into contact with the sample, solution, and the like. On the capillary cathode electrode side, the capillary 101 is fixed by a load header 203. The load header 203 is provided with an cathode electrode 114.

The optical system 104 is formed of an irradiation system and a detection system. The optical system 104 functions to irradiate, with an exciting light, a portion where the polyimide-coated film of the capillary 101 is removed, i.e. a detection portion. The detection system functions to detect fluorescence from the sample in the detection portion of the capillary 101. The sample is analyzed with the light detected by the detection system.

The pump mechanism 103 includes a syringe 108, a block 109, a check valve 110, a polymer container 111 and a anode buffer container 112. By connecting the capillary head 205 to the block 109, the capillary 101 is connected to a flow path in the block 109. By an operation on the syringe 108, a polymer in the polymer container 111 is filled into the capillary 101 or the capillary 101 is refilled with that polymer, via the flow path in block 109. The refilling of the polymer in the capillary 101 is performed at each measurement to improve the measurement performance of the capillary electrophoresis device.

A anode electrode 113 is disposed in the anode buffer container 112. The high-voltage power supply 105 applies a high voltage between the anode electrode 113 and the cathode electrode 114.

The oven 106 holds the capillary array 102 in a planar form between temperature-controlling plates mounted with an insulator and a heater to keep the temperature of the capillary constant. The temperature-controlling plates are mounted with a temperature sensor for feedback. By fixing the load header 203 of the capillary array to the oven, the tip end of the capillary head 205 can be fixed to a desired position.

The autosampler 107 is provided with three electric motors and linear guides for moving a moving stage, and thereby the moving stage is movable in three-axis directions of upward-downward, rightward-leftward and forward-backward. The moving stage can transfer the buffer container, rinse container, waste container and sample plate to the capillary cathode electrode 206 as necessary.

FIG. 2 shows the specifics of the capillary array 102 in the capillary electrophoresis device shown in FIG. 1. The capillary head 205 is provided to the one end of the capillary 101, and the capillary cathode electrode 206 is formed at the other end of the capillary 101. The load header 203 is mounted with a metallic hollow electrode. The capillary cathode electrode 206 penetrates through the hollow electrode, and protrudes from the tip end. The capillary 101 is fixed on a sheet 207. The sheet 207 is held by the load header 203. The optical system 104 includes a cone lens 208 and a reference base 204. The detection portion of the capillary 101 is held on the reference base 204. The detection portion of the capillary 101 is irradiated with an exciting light from the light source via the cone lens 208.

Figure 3A:
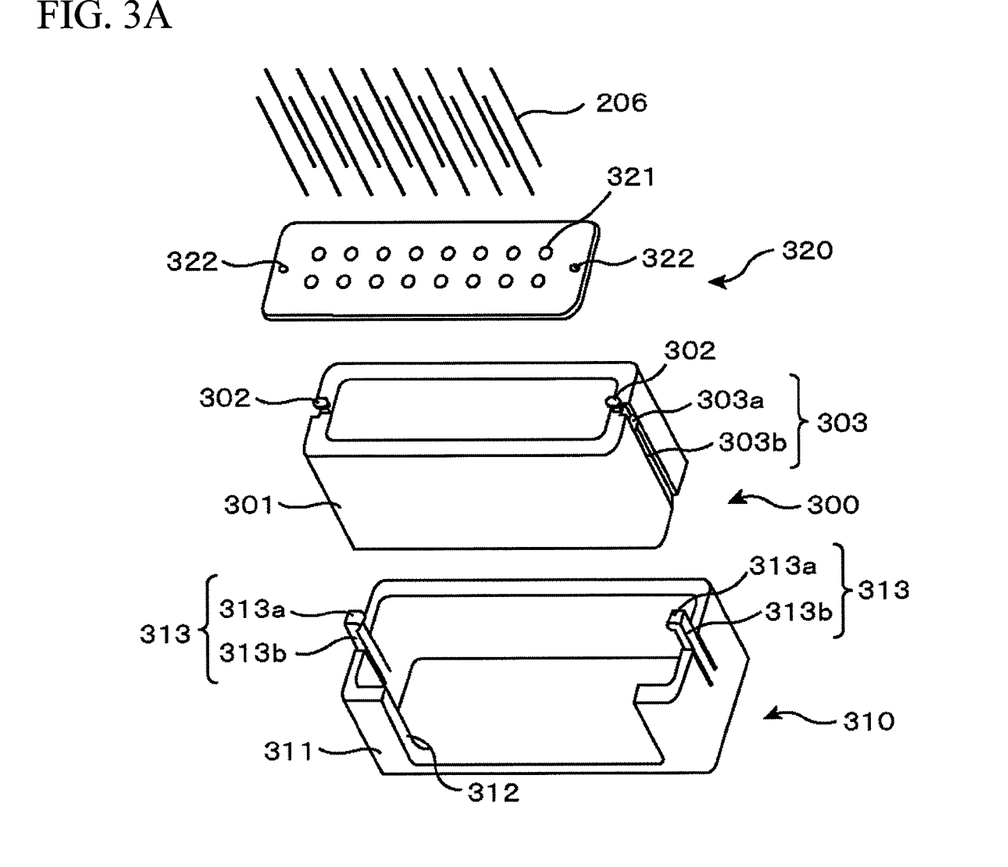
FIGS. 3A and 3B are respectively an exploded view and an assembled view of a holder for the capillary electrophoresis device according to the embodiment.

Next, description will be given of an example of a holder used for the capillary electrophoresis device of the present invention with reference to FIGS. 3A and 3B. As shown in FIG. 3A, the holder of this example includes a container 300, a container-accommodation unit 310 and a septum 320.

The container 300 includes: a reservoir 301 which stores a solution such as a sample solution, buffer solution, assy solution, and rinse; a pair of first engagement portions 302 provided on the top surface of the reservoir 301; and a pair of second engagement portions 303 formed on side surfaces of the reservoir 301. The second engagement portion 303 includes a groove 303b and a convex portion 303a formed in the groove.

The container-accommodation unit 310 includes: a holding portion 311 for holding the container 300; and a pair of engagement portions 313 protruding from the top surface of the holding portion. The engagement portion 313 includes: a boss 313b and a hook 313a formed on the tip end of the boss. A notch 312 is formed in the holding portion 311.

The septum 320 includes capillary holes 321 through which the capillaries penetrate; and engagement portions which engage with the first engagement portions 302. The engagement portion includes a through hole 322. The septum 320 is made of an elastic material such as a rubber or a resin.

Figure 3B:
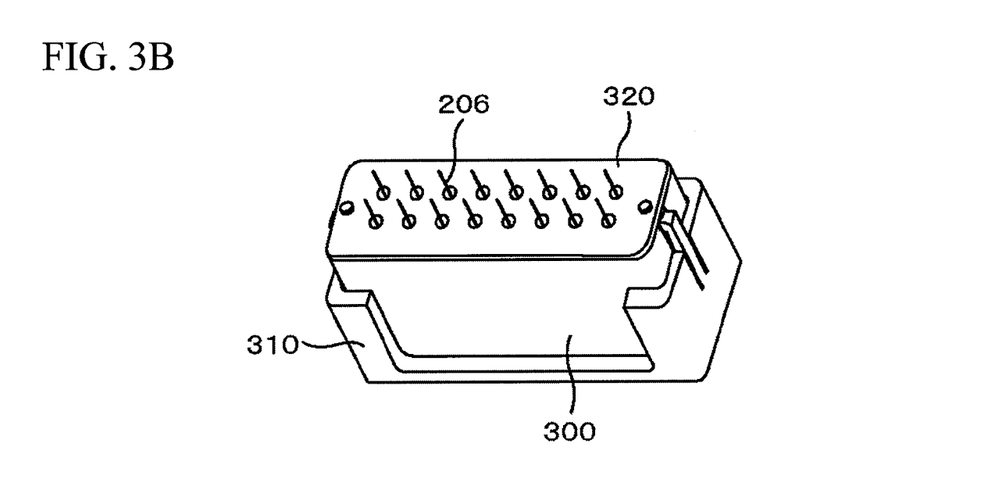

FIG. 3B shows the assembled holder of this embodiment. In the holder, the container 300 is accommodated in the container-accommodation unit 310, and the septum 320 is mounted on the container 300 so as to hermitically seal the top surface of the container 300. In FIGS. 3A and 3B, the single container 300 is accommodated in the container-accommodation unit 310; however, the multiple containers 300 may be accommodated therein, while being arranged in line. For example, when the three containers 300 are accommodated, the interior size of the container-accommodation unit 310 should be designed to accommodate the three containers 300.

Next, description will be given of a capillary-drawing direction as well as a direction in which the container 300 is put into container-accommodation unit 310. In the capillary electrophoresis device of this embodiment, the capillary-drawing direction is perpendicular to a direction in which the septum 320 lies. In other words, the capillary-drawing direction is parallel to the depth direction of the container-accommodation unit 310. Meanwhile, the direction in which the container 300 is put into the container-accommodation unit 310 is the same as the capillary-drawing direction. In this embodiment, the container 300 is put into the container-accommodation unit 310 from the top of the unit 310. Thus, the direction in which the container 300 is put is the same as the capillary-drawing direction.

Figure 4A:
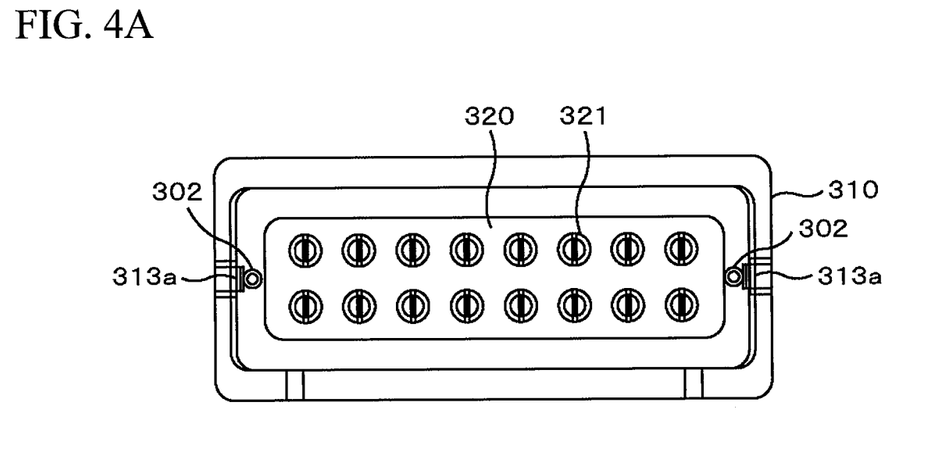
FIGS. 4A and 4B show the holder in use for the capillary electrophoresis device according to the embodiment.
Figure 4B:
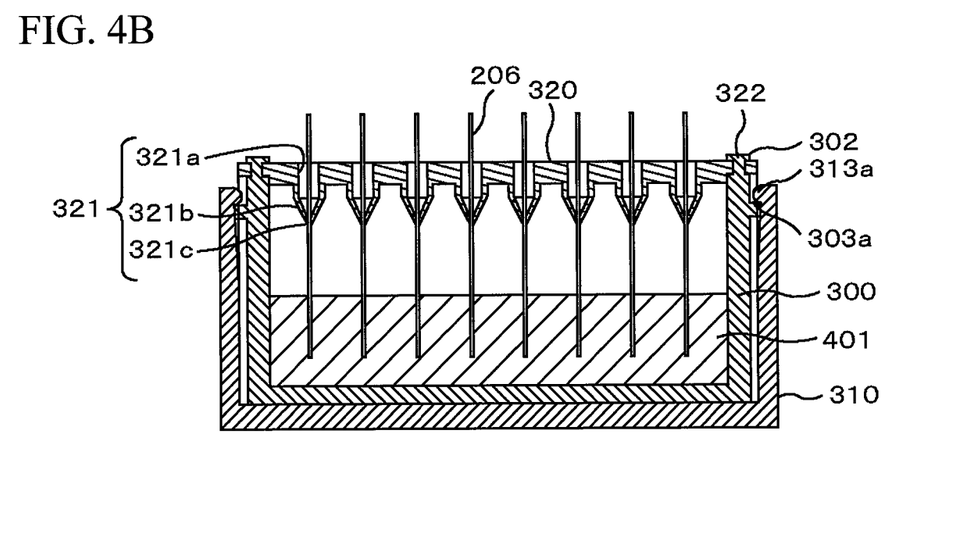

FIGS. 4A and 4B show the holder in use according to the embodiment. The first engagement portions 302 of the container 300 penetrate into the holes 322 in the septum 320. The hooks 313a of the container-accommodation unit 310 engage with the convex portions 303a of the container 300. As illustrated, the reservoir 301 stores a solution 401 such as a buffer solution, assy solution, rinse, and washing waste.

The capillary hole 321 in the septum 320 includes: a cylinder-shaped concave portion 321a; a cone-shaped bottom portion 321b; and a through hole 321c formed at the lower end of the bottom portion 321b. The through hole 321c may be formed of a thin film with a cut in a straight line. The concave portion 321a and the bottom portion 321b are formed so as to protrude from the bottom surface of the septum 320.

When the capillary cathode electrode 206 is inserted into the capillary hole 321 of the septum 320, the septum 320 receives a downward force due to a friction force between the capillary cathode electrode 206 and the through hole 321c. Nevertheless, since the periphery of the septum 320 is supported by the top surface of the container 300, the septum 320 would not be moved further downward.

When the capillary cathode electrode 206 is pulled out from the capillary hole 321 in the septum 320, the septum 320 receives an upward force due to a friction force between the capillary cathode electrode 206 and the through hole 321c.

Nevertheless, since the holes 322 in the septum 320 and the first engagement portions 302 of the container 300 engage with each other, the septum 320 would not move upward away from the container 300. When the capillary cathode electrode 206 is pulled out from the capillary hole 321 in the septum 320, the container 300 also receives an upward force due to the friction force between the capillary cathode electrode 206 and the through hole 321c. Nevertheless, since the convex portions 303a of the container 300 and the hooks 313a of the container-accommodation unit 310 engage with each other, the container 300 would not be moved upward away from the container-accommodation unit 310.

In this manner, according to this embodiment, even when the capillary cathode electrode 206 is inserted into the capillary hole 321 in the septum 320, and even when the capillary cathode electrode 206 is pulled out from the capillary hole 321 in the septum 320, the septum 320 and the container 300 never moves.

The septum 320 is made of a rubber-like elastic material. Accordingly, when the capillary cathode electrode 206 is not inserted into the capillary hole 321 in the septum 320, the capillary hole 321 is being contracted and closed due to the elastic force. Meanwhile, when the capillary cathode electrode 206 is inserted into the capillary hole 321 in the septum 320, the hole 321 also contracts due to the elastic force to hermetically seal the clearance between the hole 321 and the capillary cathode electrode 206. Thus, the interior of the container 300 is hermetically sealed all the time.

In this embodiment, the concave portion 321a and the bottom portion 321b are formed to protrude downward from the bottom surface of the septum 320, and the through hole 321c is formed in the bottom portion 321b. Accordingly, this embodiment has an advantage of facilitating the expansion and the contraction of the through hole 321

Figure 5A:
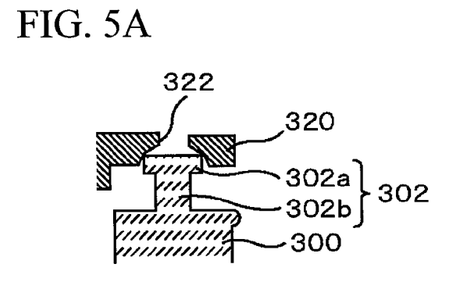
FIGS. 5A to 5D illustrate a method for assembling a holder for a capillary electrophoresis device according to the embodiment.
Figure 5B:
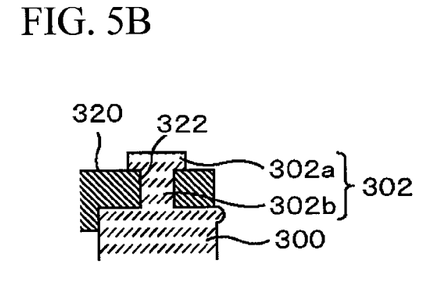

With reference to FIGS. 5A to 5D, description will be given of a method for assembling the container 300 and the septum 320 together with the container-accommodation unit 310. The first engagement portion 302 of the container 300 includes a head 302a and a constriction 302b. The head 302a and the constriction 302b have circular cross sections. The outer diameter of the head 302a is larger than that of the constriction 302b. As shown in FIG. 5A, the septum 320 is disposed on the top surface of the container 300 so that the hole 322 in the septum 320 can engage with the head 302a of the first engagement portion 302 on the container 300. When the septum 320 is pushed onto the container 300, the inner diameter of the hole 322 in the septum 320 is elastically deformed and enlarged. When the septum 320 is further pushed onto the container 300, the inner diameter of the hole 322 in the septum 320 is enlarged so that the head 302a can pass through the hole 322. After the head 302a of the first engagement portion 302 on the container 300 passes through the hole 322, the inner diameter of the hole 322 in the septum 320 returns to the original size. As shown in FIG. 5B, the hole 322 in the septum 320 engages with the constriction 302b of the first engagement portion 302 on the container 300.

Figure 5C:
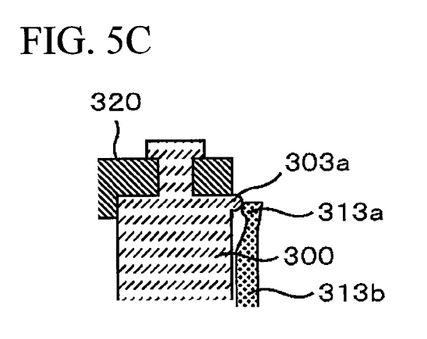
Figure 5D:
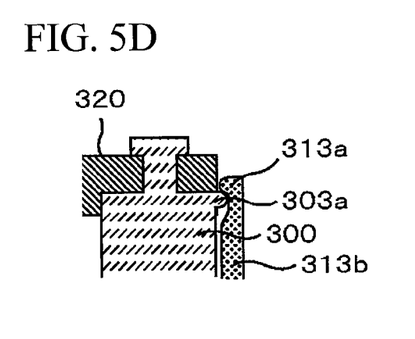

When the container 300 is inserted into the container-accommodation unit 310 as shown in FIG. 5C, the hook 313a of the container-accommodation unit 310 comes into contact with the convex portion 303a of the container 300. When the container 300 is further inserted into the container-accommodation unit 310, the hook 313a of the container-accommodation unit 310 is elastically deformed to ride over the convex portion 303a of the container 300. As shown in FIG. 5D, after the hook 313a of the container-accommodation unit 310 rides over the convex portion 303a of the container 300, the hook 313a, as well as the container-accommodation unit 310 returns to the original shapes. In this manner, the second engagement portions 303 of the container 300 engage with the engagement portions 313 of the container-accommodation unit 310. In this state, even if the container 300 receives a force such that the container 300 may be lifted and separated from the container-accommodation unit 310, the container 300 will not be separated from the container-accommodation unit 310, since the convex portions 303a of the container 300 are engaged with the hooks 313a of the container-accommodation unit 310.

According to the holder for the capillary electrophoresis device of the present invention, when the capillary is pulled out from the septum, the taking off of the septum from the container and the taking off of the container from the container-accommodation unit are certainly prevented, since the holes 322 in the septum 320 and the first engagement portions 302 on the container 300 engage with each other.

According to the holder for the capillary electrophoresis device of this embodiment, the hole 322 is formed in the septum 320 so as to protrude downward from the bottom surface of the septum 320. Thereby, the hole 322 is elastically deformed only slightly. Therefore, only the minimum external force should be applied to engage the holes 322 in the septum 320 with the first engagement portions 302 on the container 300. Moreover, when the capillary is inserted or pulled out, the friction force between the capillary and the hole in the septum is small, and the capillary is inserted or pulled out with a small force.

According to the holder for the capillary electrophoresis device of this embodiment, the septum is mounted on the container in the capillary-drawing direction, and the container is inserted into the container-accommodation unit in the capillary-drawing direction. Thus, in a case where the multiple containers are accommodated in the container-accommodation unit, any one of the containers can be put in or out in any order. Therefore, the controllability of the holder is improved.

Description will be given of examples of engagement portions of the container and the septum in a holder for the capillary electrophoresis device according to another embodiment with reference to FIGS. 6A to 6D. The holders in these examples include the container 300, the container-accommodation unit 310 and the septum 320. The septum 320 is provided with the capillary holes 321 through which the capillaries penetrate. The way of inserting the container 300 into the container-accommodation unit 310 is the same as that in the example in FIG. 5.

Figure 6A:
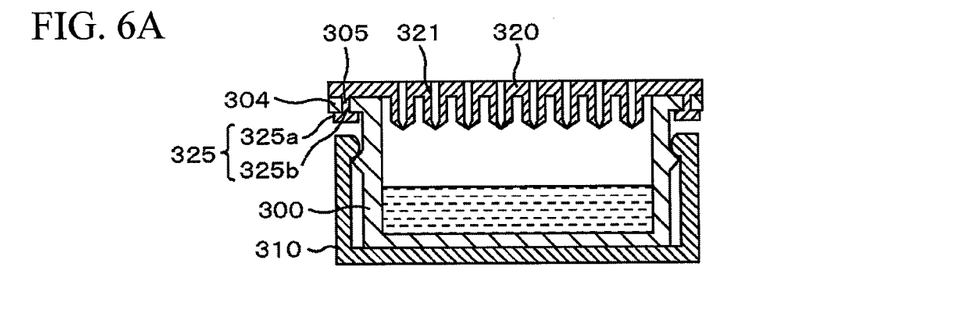
FIGS. 6A to 6D show examples of engagement portions of a container and a septum in the holder for the capillary electrophoresis device according to another embodiment.

In the example shown in FIG. 6A, a hole 305 is formed in a flange 304 on an upper end of the container 300. An engagement portion 325 is provided to the septum 320. The engagement portion 325 is a boss including a head 325a and a constriction 325b. This boss extends downward from the septum 320, that is, in the direction of the gravitational force. The constriction 325b of the engagement portion 325 engages with the hole 305 of the container 300, and the head 325a of the engagement portion 325 protrudes from the hole 305 of the container 300. By engaging the engagement portion 325 of the septum 320 with the hole 305 of the container 300, the septum 320 is held by the container 300.

Figure 6B:
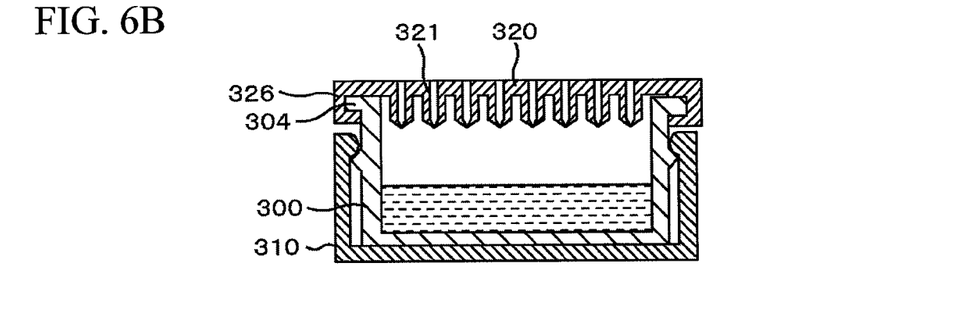
Figure 6C:
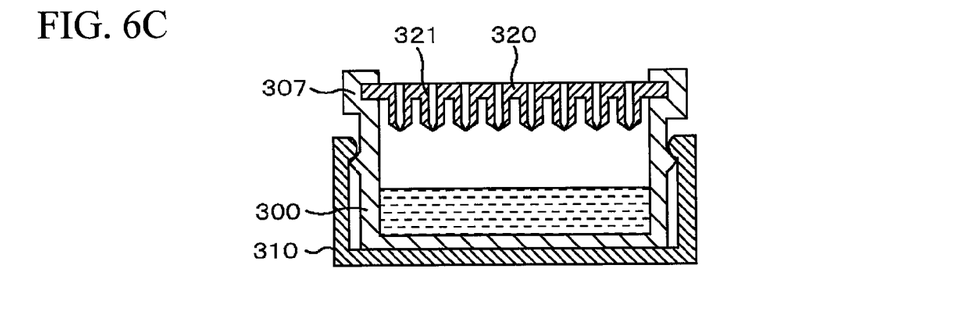

In the example shown in FIG. 6B, a gripper 326 is formed on an edge portion of the septum 320. By engaging the gripper 326 of the septum 320 with the flange 304 on the upper end of the container 300, the septum 320 is held by the container 300. In the example shown in FIG. 6C, a gripper 307 is formed on an upper end of the container 300. By engaging an edge portion of the septum 320 with the gripper 307 of the container 300, the septum 320 is held by the container 300.

Figure 6D:
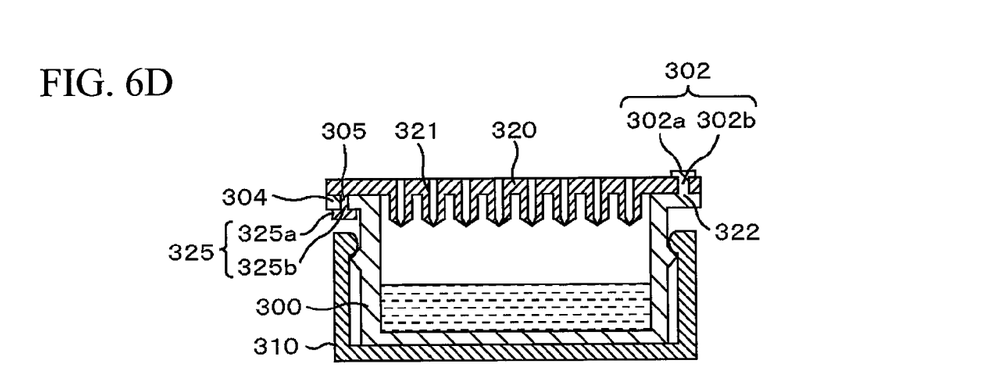

The structure shown in FIG. 6D is in combination of the examples shown in FIG. 6A and FIGS. 5A to 5D, and is a left-right asymmetrical structure. Specifically, the septum 320 is provided, on one end thereof, with the engagement portion 325 that is the boss including the head 325a and the constriction 325b. The hole 305 is formed in the flange 304 of the container 300. The engagement portion 325 of the septum 320 engages with the hole 305 of the container 300. On the other end of the septum 320, the container 300 is provided, on the upper end thereof, with the engagement portion 302 that is the boss including the head 302a and the constriction 302b. The septum 320 is provided with the hole 322. The head 302a of the engagement portion 302 on the container 300 engages with the hole 322 in the septum 320.

In the examples of the engagement portions of the container and the septum shown in FIGS. 6A to 6D, when the capillary is pulled out from the septum, the detachment of the septum from the container and the detachment of the container from the container-accommodation unit are certainly prevented, since the septum 320 and the container 300 engage with each other. Furthermore, since the capillary hole 321 in the septum 320 does not deform, this makes the friction between the capillary hole 321 and the capillary minimum. Therefore, the capillary is easily pulled out from the septum.

The same holds true for a case where the capillary is inserted into the septum in addition to the case where the capillary is pulled from the septum. Specifically, when the capillary is inserted into the septum, the capillary hole 321 in the septum 320 does not deform. Thus, this allows the friction between the capillary hole 321 and the capillary minimum. Therefore, the capillary is easily inserted into the septum.

The present invention is not limited to the above embodiments. Those skilled in the art would easily understand that various modifications can be made within the scope of the invention described in the section of claims.

What is claimed is:

1. A capillary electrophoresis device comprising:
   a capillary;
   a power supply for applying a high voltage to both ends of the capillary;
   an optical system for irradiating a sample separated by electrophoresis in the capillary with an exciting light to detect fluorescence from the sample;
   a holder in which any one of the sample and a solution is stored; and
   an autosampler for transferring the holder, wherein the holder includes:
      a container having a plurality of wells for storing the any one of the sample and the solution;
      a septum having a capillary hole through which the capillary penetrates and is made of an elastic deformable material for covering the holder; and
      a container-accommodation unit for holding the container and covering a bottom surface and side surface of the container, wherein:
      the container includes a first engagement portion formed on the top surface thereof and a second engagement portion including a convex portion formed on a side surface thereof,
      the container-accommodation unit has an elastic deformable boss on a top surface thereof,
      the first engagement portion is provided in a periphery of the plurality of wells,
      the septum has a third engagement portion engaging with the first engagement portion,
      either the first engagement portion or the third engagement portion has a boss including a head and a constriction and the other of the first engagement portion and the third engagement portion has a hole,
      the boss has a T-shaped cross section,
      the constriction engages the hole of the first engagement portion or the third engagement portion by elastic deformation of the septum, and the head protrudes from the hole, so that the septum is held to cover the container, and
      the second engagement portion engages with the boss of the container-accommodation unit by the elastic deformation.

2. The capillary electrophoresis device according to claim 1, wherein the first engagement portion has the boss and the third engagement has the hole.

3. The capillary electrophoresis device according to claim 1, wherein the first engagement portion has the hole and the third engagement portion has the boss.

4. The capillary electrophoresis device according to claim 2, wherein
   the boss of the first engagement portion protrudes in a direction in which the capillary is inserted into or pulled out from the capillary hole.

5. The capillary electrophoresis device according to claim 3, wherein
   the boss of the engagement portion protrudes in a direction in which the capillary is inserted into or pulled out from the capillary hole.

6. The capillary electrophoresis device according to claim 1, wherein
   the elastic deformable boss of the container-accommodation unit includes a hook made of an elastic deformable material at a tip of the engagement portion and the hook engages with the convex portion of the container.

7. The capillary electrophoresis device according to claim 1, wherein
   directions in which the capillary is inserted into and pulled out from the capillary hole are the same as directions in which the container is put in and out from the container-accommodation unit.

8. The capillary electrophoresis device according to claim 1, wherein
   the capillary hole is formed of:
      a cylinder-shaped concave portion formed in the septum; a cone-shaped bottom portion; and
      a through hole formed at a tip end of the bottom portion, and the capillary hole protrudes downward from the bottom surface of the septum.

9. A method for assembling a holder for a capillary electrophoresis device, the holder including:
   a container having a plurality of wells for storing the any one of the sample and the solution;
   a septum having a capillary hole through which the capillary penetrates and is made of an elastic deformable material for covering the holder; and
   a container-accommodation unit for holding the container and covering a bottom surface and side surface of the container, wherein:
   the container includes a first engagement portion formed on the to surface thereof and a second engagement portion including a convex portion formed on a side surface thereof,
   the container-accommodation unit has an elastic deformable boss on a top surface thereof,
   the first engagement portion is provided in a periphery of the plurality of wells,
   the septum has a third engagement portion engaging with the first engagement portion, either the first engagement portion or the third engagement portion has a boss including a head and a constriction and the other of the first engagement portion and the third engagement portion has a hole, the boss has a T-shaped cross section, the constriction engages the hole of the first engagement portion or the third engagement portion by elastic deformation of the septum, and the head protrudes from the hole, so that the septum is held to cover the container, and the second engagement portion engages with the boss of the container-accommodation unit by the elastic deformation, the method comprising steps of:

covering the container with the septum in a way that the engagement portion of the septum engages with the first engagement portion of the container; and accommodating the container into the container-accommodation unit in a way that the second engagement portion of the container engages with the engagement portion of the container-accommodation unit, wherein a direction in which the container is accommodated into the container-accommodation unit is the same as a direction in which the capillary is inserted into and pulled out from the capillary hole.

10. The method for assembling a holder for a capillary electrophoresis device according to claim 9, wherein the direction in which the container is accommodated into the container-accommodation unit is the direction of the gravitational force.

11. The method for assembling a holder for a capillary electrophoresis device according to claim 9, wherein the first engagement portion has the boss and the third engagement portion has the hole.

12. The method for assembling a holder for a capillary electrophoresis device according to claim 9, wherein the elastic deformable boss of the container-accommodation unit includes a hook made of an elastic deformable material at a tip of the engagement portion and the hook engages with the convex portion of the container.

13. A holder comprising:

a container having a plurality of wells for storing the any one of the sample and the solution;

a septum having a capillary hole through which the capillary penetrates and is made of an elastic deformable material for covering the holder; and a container-accommodation unit for holding the container and covering a bottom surface and side surface of the container, wherein:

the container includes a first engagement portion formed on the to surface thereof and a second engagement portion including a convex portion formed on a side surface thereof, the container-accommodation unit has an elastic deformable boss on a top surface thereof, the first engagement portion is provided in a periphery of the plurality of wells, the septum has a third engagement portion engaging with the first engagement portion, either the first engagement portion or the third engagement portion has a boss including a head and a constriction and the other of the first engagement portion and the third engagement portion has a hole, the boss has a T-shaped cross section, the constriction engages the hole of the first engagement portion or the third engagement portion by elastic deformation of the septum, and the head protrudes from the hole, so that the septum is held to cover the container, and the second engagement portion engages with the boss of the container-accommodation unit by the elastic deformation.

14. The holder according to claim 13, wherein the boss of the container includes a head and a constriction, and when the boss of the container engages with the hole in the septum, the constriction of the container engages with the hole in the septum, and the head protrudes from the hole in the septum.

15. The holder according to claim 13, wherein the boss of the container-accommodation unit having a hook at a tip end thereof, the container is provided at a side surface thereof with a convex portion, and the hook of the container-accommodation unit engages with the convex portion of the container.

16. The holder according to claim 15, wherein a groove for engaging with the boss of the container-accommodation unit is formed in the side surface of the container, and the convex portion is formed in the groove.

17. The holder according to claim 13, wherein directions in which the capillary is inserted into and pulled out from the capillary hole are the same as directions in which the container is put in and out from the container-accommodation unit.

18. The holder according to claim 13, wherein a direction in which the capillary inserted into the capillary hole is the direction of the gravitational force.

19. The holder according to claim 13, wherein the capillary hole is formed of: a cylinder-shaped concave portion formed in the septum; a cone-shaped bottom portion; and a through hole formed at a tip end of the bottom portion, and the capillary hole protrudes downward from the bottom surface of the septum.

20. The holder according to claim 19, wherein the through hole is formed of a film with a cut in a straight line.

21. The holder according to claim 13, wherein the septum is made of an elastic material.

22. The holder according to claim 13, wherein the capillary hole in the septum is closed due to an elastic force when the capillary is out of the capillary hole.

* * * * *